(12) United States Patent
Williams

(10) Patent No.: US 6,202,689 B1
(45) Date of Patent: Mar. 20, 2001

(54) FLUID-COLLECTING RECEPTACLE HAVING HINGED UPPER SHEET

(76) Inventor: Kevin M. Williams, 35 McGrath Dr., Middletown, CT (US) 06457

(*) Notice: Subject to any disclaimer, the term of this patent is extended or adjusted under 35 U.S.C. 154(b) by 0 days.

(21) Appl. No.: 09/626,807

(22) Filed: Jul. 27, 2000

Related U.S. Application Data

(62) Division of application No. 09/114,430, filed on Jul. 13, 1998, now Pat. No. 6,102,073.

(51) Int. Cl.⁷ ..................................................... A61M 1/00
(52) U.S. Cl. ..................... 137/602; 137/561 R; 137/312; 137/362; 604/356
(58) Field of Search ................................ 137/561 R, 602, 137/312, 313, 362; 4/583, 582, 581; 296/97.23; 604/356; 5/606, 620, 630

(56) References Cited

U.S. PATENT DOCUMENTS

| | | |
|---|---|---|
| 868,137 | 10/1907 | Shriver . |
| 1,501,739 | 7/1924 | Benedek . |
| 1,613,158 | 1/1927 | Brewer . |
| 1,618,165 | 2/1927 | Boschelli . |
| 1,948,327 | 2/1934 | Berwick . |
| 2,515,450 | 7/1950 | Hull . |
| 2,546,394 | 3/1951 | Harmon . |
| 2,599,049 | 6/1952 | Dollinger . |
| 2,650,855 | 9/1953 | Peirce . |
| 2,733,684 | 2/1956 | Trenchard . |
| 3,082,032 | 3/1963 | Stata . |
| 3,418,668 | 12/1968 | Anderson et al. . |
| 3,605,166 | 9/1971 | Chen . |
| 3,757,356 | 9/1973 | Freeman . |
| 4,243,214 | 1/1981 | LaRooka . |
| 4,280,729 | 7/1981 | Morawski . |
| 4,420,180 | 12/1983 | Dupont et al. . |
| 4,679,590 | 7/1987 | Hergenroeder . |
| 4,729,404 | 3/1988 | Hergenroeder . |
| 4,889,155 | 12/1989 | Trotter . |
| 4,903,723 | 2/1990 | Sublett . |
| 4,931,330 | 6/1990 | Stier et al. . |
| 5,204,159 | 4/1993 | Tan . |
| 5,452,739 | 9/1995 | Mustee et al. . |

Primary Examiner—John Rivell
(74) Attorney, Agent, or Firm—Rankin, Hill, Porter & Clark LLP

(57) ABSTRACT

A fluid-collecting receptacle includes a fluid-impervious base sheet having an upstanding perimeter lip, a sloping floor, and a fluid outlet in the floor. A porous support member is disposed atop the upper surface of the base sheet and a porous, flexible mat is disposed atop the porous support member. Openings in the mat and the porous support member permit fluid to be discharged onto the sloping floor where removal through the fluid outlet can be accomplished by means of a suction device. The device can be equipped with suction cups to prevent slippage or a rigidified foam core to strengthen the device and prevent slippage. In an alternative embodiment, the porous support member and the mat are replaced by a hinged sheet formed of a plurality of small basins each having a drain opening.

8 Claims, 4 Drawing Sheets

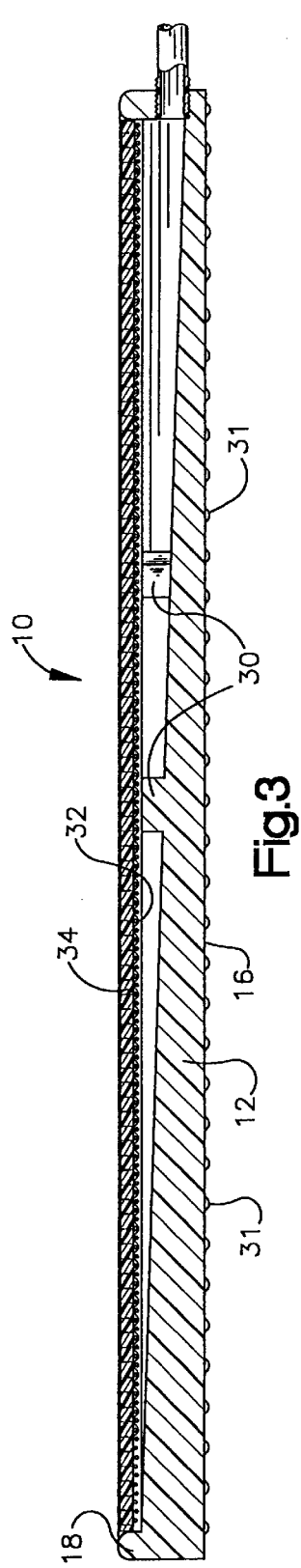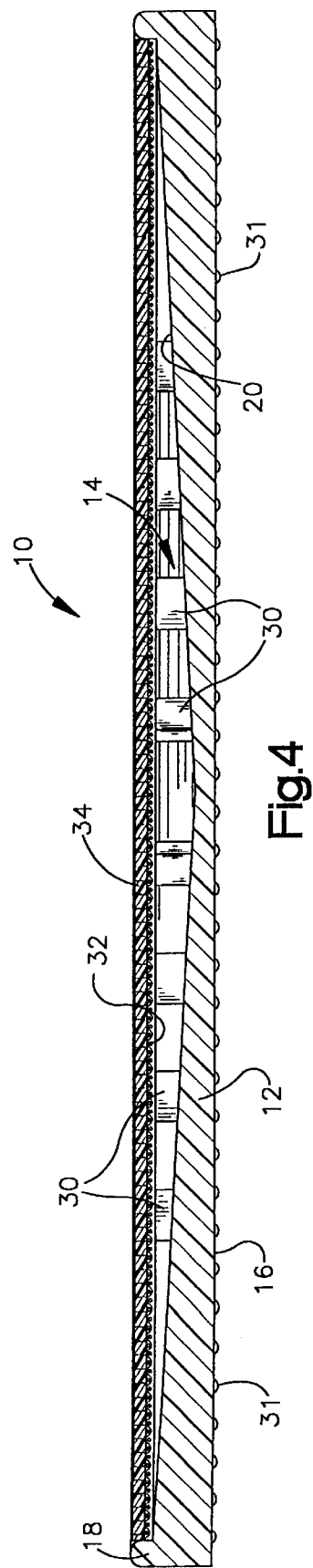

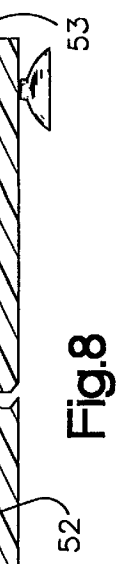
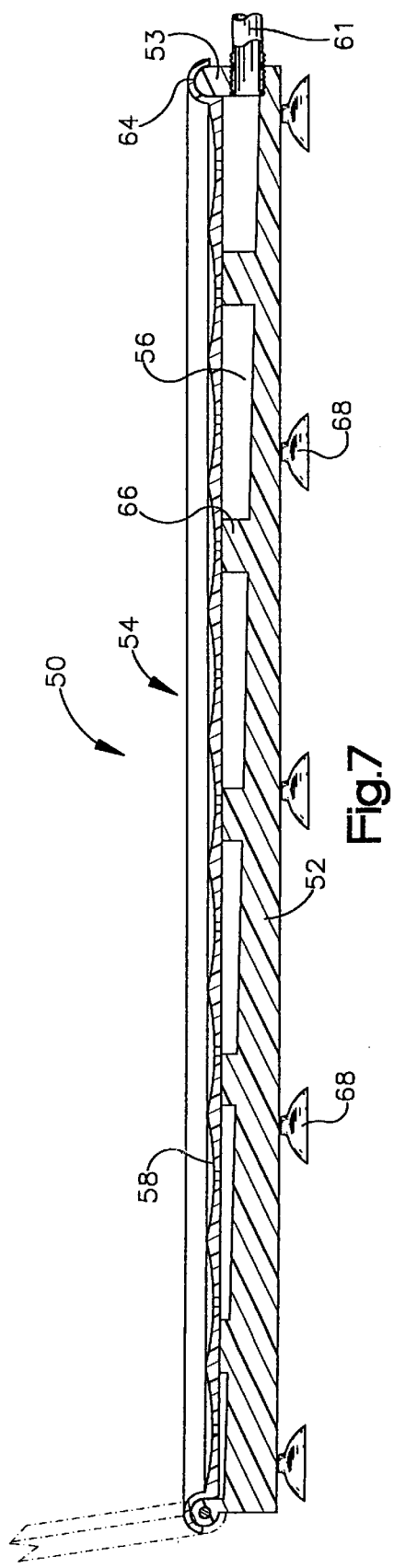
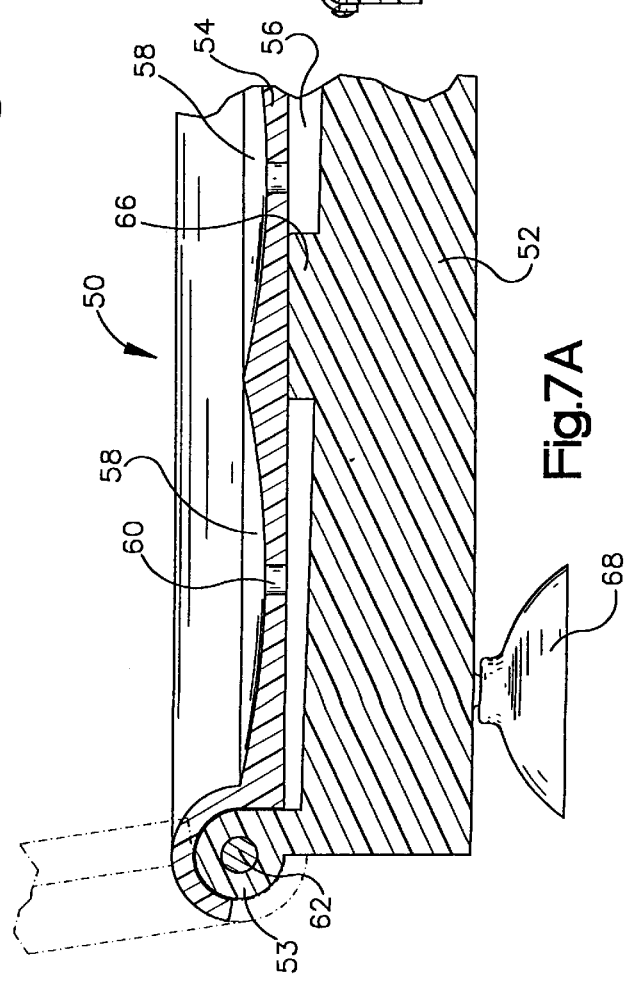

FLUID-COLLECTING RECEPTACLE HAVING HINGED UPPER SHEET

This application is a division of application Ser. No. 09/114,430, filed Jul. 13, 1998 now U.S. Pat. No. 6,102,073.

BACKGROUND OF THE INVENTION

1. Field of the Invention

The invention relates to a receptacle for collecting fluid and, more particularly, to a receptacle especially suitable for use in an operating room where large quantities of fluid may be present.

2. Description of the Prior Art

In the course of conducting surgical procedures such as arthroscopic surgery, high pressure saline solution is introduced into the surgical site to displace blood and to distend the joint. This high pressure saline solution also stops bleeding due to high pressure closure of blood vessels. In the course of an arthroscopic surgical procedure, large quantities of saline solution tend to escape and typically run onto the operating room floor, notwithstanding attempts to collect the flow by using towels or plastic sheets draped in various ways. The use of towels or sheets to collect or divert fluid is an exceedingly ineffective technique. It is entirely possible that saline solution will not be collected and will cover the floor, possibly causing operating room personnel to slip. Also, it will be more difficult to clean up after a surgical procedure with saline solution on the floor.

Depending on the type of operation and its duration, a large quantity of saline solution may be lost. It is not uncommon to use between one and eight two-liter bags of saline solution during the course of a surgical procedure.

One approach to the problem is disclosed by the patent to Hergenroeder, U.S. Pat. No. 4,679,590. The '590 patent discloses a thin mat that is placed on the operating room floor. The mat includes a gridwork of small basins that form collecting surfaces with drains. Fluid that flows through the drains enters channels that are formed between the mat and the floor (in effect, the floor is part of the device). A suction device such as an aspirator is connected to the channels so as to withdraw fluid contained therein.

A drawback of the device disclosed in the '590 patent is that it requires that fluidtight contact be maintained between the perimeter of the mat and the floor. If the floor should contain defects, it is possible that adequate fluid-removal performance might not be possible. Yet another problem not adequately addressed by the device in question is that of slippage. It is possible that the large amount of fluid contained beneath the surface of the mat might lead to unexpected movement thereof during the course of a surgical procedure.

SUMMARY OF THE INVENTION

In response to the foregoing concerns, the present invention provides a new and improved fluid-collecting receptacle especially adapted for use in conjunction with arthroscopic surgery procedures. The invention includes a solid base sheet of rigid, fluid-impervious material. The base sheet includes an upstanding perimeter lip, a sloping floor that creates a reservoir, and an outlet at the lowest point of the reservoir along one side of the base sheet. A porous support member is disposed atop the upper surface of the base sheet, and a porous, flexible mat is disposed atop the porous support member. In the preferred embodiment, the base sheet includes a plurality of protuberances projecting upwardly, the upper surfaces of which lie in a common plane. The porous support member rests on top of the protuberances. The mat and the porous support member each can be a generally planar member or they can be foldable for purposes of cleaning and storage.

If desired, the underside of the base sheet can be formed with a cavity that is filled with a solidified core of a foamed plastics material. The foamed core provides rigidity to the sheet and assists in preventing slippage thereof on the operating room floor. In order to enhance the non-slip characteristics of the device, a non-slip material can be applied to the bottom of the base sheet or its solidified core. Alternatively, it is possible for a plurality of suction cups to be attached to the underside of the base sheet, thereby also preventing slippage.

In an alternative embodiment of the invention, a first, lower sheet is formed of a fluid-impervious material. The sheet includes an upstanding perimeter lip. The sheet includes a sloping floor and a fluid outlet at the lowest point of the sloping floor. A second, upper sheet formed of fluid-impervious material is spaced from the upper surface of the second sheet so as to define a reservoir therebetween. The second sheet includes a plurality of small basins, each having a drain opening at the lowest point thereof through which fluid can be discharged into the reservoir. The second sheet is hingedly connected to the perimeter lip along one edge, and rests atop the remaining portions of the lip. The second sheet thus is movable from a first, closed position where a user can stand on the sheet to a second, open position where access can be had to the reservoir.

The foregoing, and other features of the invention will be apparent from the following description and claims.

BRIEF DESCRIPTION OF THE DRAWINGS

FIG. 3 is a cross-sectional view of the receptacle of FIG. 1 taken along a plane indicated by line 3—3 in FIG. 2;

FIG. 4 is a cross-sectional view of the receptacle of FIG. 1 taken along a plane indicated by line 4—4 in FIG. 2;

FIG. 7 is a cross-sectional view of the invention of FIG. 6 taken along a plane indicated by line 7—7 in FIG. 6;

FIG. 7A is an enlarged view of a portion of FIG. 7; and

FIG. 8 is a cross-sectional view of the invention of FIG. 6 taken along a plane indicated by line 8—8 in FIG. 6.

DESCRIPTION OF THE PREFERRED EMBODIMENT

Figure 1:
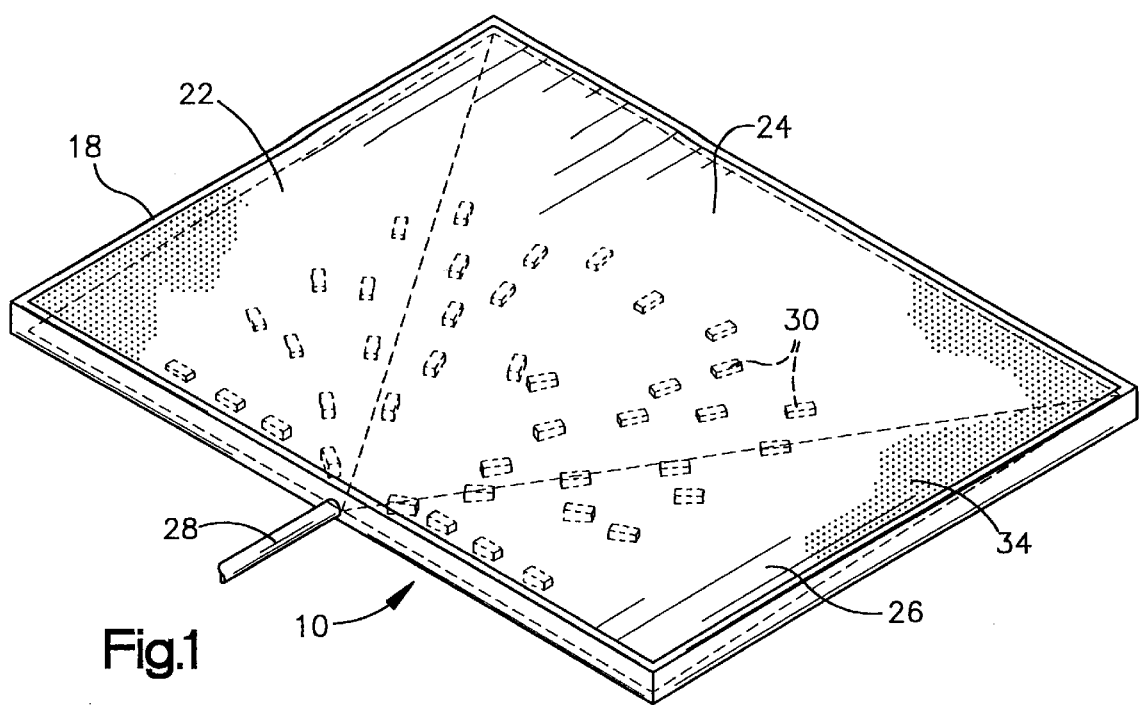
FIG. 1 is a perspective view of a fluid-collecting receptacle according to the invention.
Figure 2:
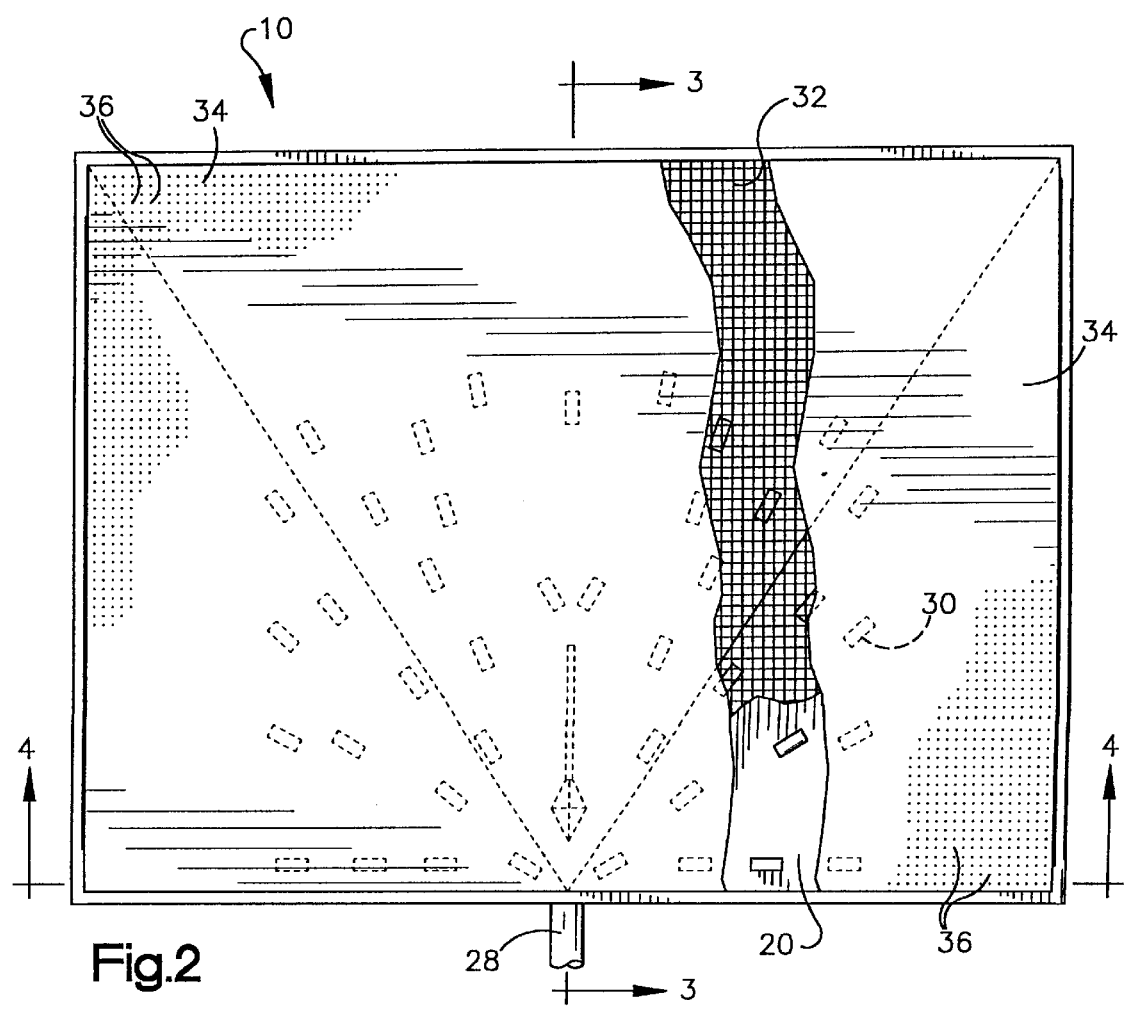
FIG. 2 is a top plan view of the receptacle of FIG. 1 with portions thereof broken away and removed for clarity of illustration.

Referring to FIGS. 1–5, a fluid-collecting receptacle according to the invention is indicated generally by the reference numeral 10. The receptacle 10 includes a base sheet 12 made of a fluid-impervious material. Typically, the base sheet 12 would be made of a plastics material such as polyethylene, polypropylene, or other material suitable for injection molding. The base sheet 12 has an upper surface 14 and a lower surface 16. An upstanding lip 18 forms the perimeter of the base sheet 12. If desired, the base sheet 12 could define a cavity (not shown) and a rigidified foam core could fill the cavity. Such a construction would provide a lighter base sheet 12 while preserving its strength. The foam core also could assist in preventing slippage of the receptacle 10.

The upper surface 14 defines a floor 20 formed of three planar segments 22, 24, 26. The segments 22, 24, 26 form a sloping surface along which fluid will flow. A fluid outlet 28 is disposed at the lowest position of the floor 20, at the intersection of the segments 22, 24, 26. A plurality of protuberances 30 extend upwardly from the surface of the floor 20. The upper surfaces of the protuberances 30 lie in a common plane. A plurality of nubs 31 project a short distance from the lower surface 16. The nubs 31 provide a small gap between the lower surface 16 and the floor upon which the receptacle 10 rests.

A porous support member 32 in the form of a grid is disposed atop the protuberances 30. The grid 32 provides support for a person standing on the receptacle 10 without permitting excessive flexing or movement. The grid 32 can be made of a strong material such as aluminum or a sturdy, injection-moldable plastics material such as ABS. As illustrated, the grid 32 is made of a strong metal screen.

A porous, flexible mat 34 having a plurality of openings 36 is disposed atop the grid 32. The mat 34 preferably is made of rubber or a rubber-like material. The mat 34 provides comfort for the user and prevents slippage. As will be apparent from an examination of FIGS. 1–4, any fluid that is directed onto the upper surface of the mat 34 will flow through the openings 36, through the grid 32, and onto the floor 20. The fluid will flow to the fluid outlet 28 where it will be withdrawn by a suitable suction device (not shown).

Figure 5:
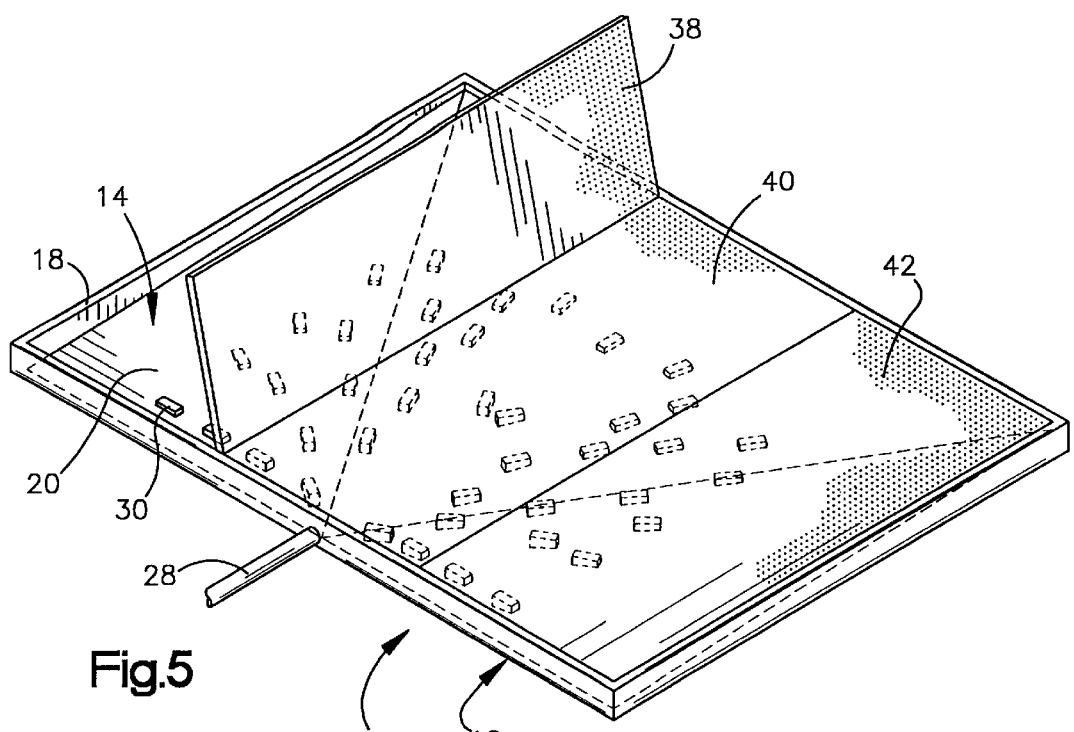
FIG. 5 is a view similar to FIG. 1 showing a mat portion thereof in a partially folded position.

It is expected that the grid 32 and the mat 34 each will be an undivided planar member without seams or segments. However, the grid 32 and the mat 34 do not have to be constructed in this manner. Referring particularly to FIG. 5, the grid 32 and the mat 34 are shown as being formed of three hinged segments 38, 40, 42. The segments can be folded for convenient storage or cleaning.

In order to prevent slippage of the receptacle 10, a plurality of suction cups (FIGS. 7, 7A, and 8) can be attached to the lower surface 16. If desired, a non-slip substance such as colloidal silica, silicon dioxide or the like can be applied to the lower surface 16 and the nubs 31 or to the foam core, if such a core is utilized.

Figure 6:
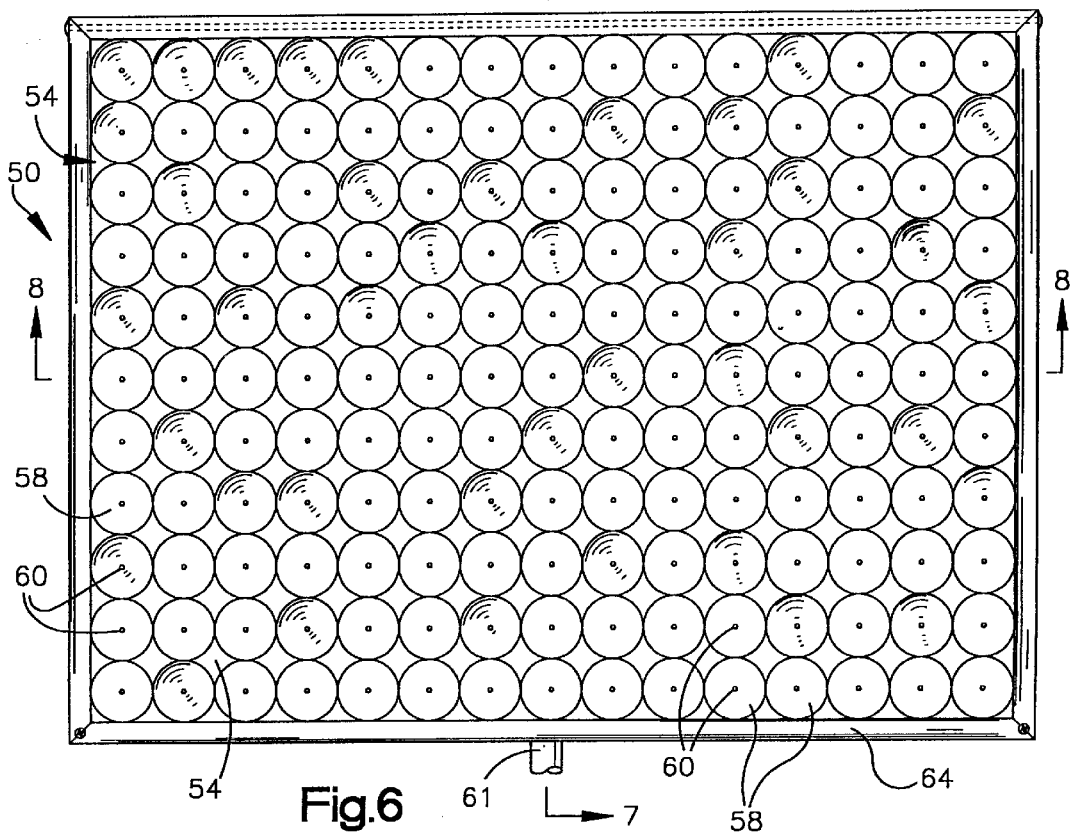
FIG. 6 is a top plan view of another alternative embodiment of the invention.

An alternative embodiment of the invention is shown in FIGS. 6–8 and is indicated by the reference numeral 50. The receptacle 50 includes a fluid-impervious base sheet 52 similar in construction to the base sheet 12. The base sheet 52 has a perimeter lip 53. An upper sheet 54 is spaced from the upper surface of the base sheet 52 so as to define a reservoir 56 therebetween. The upper sheet 54 includes a plurality of small basins 58 each having a drain opening 60 at the lowest point thereof through which fluid can be discharged into the reservoir 56. A fluid outlet 61 is disposed at the lowest position of the reservoir 56 in order to provide a drain for the reservoir 56.

The upper sheet 54 is connected to the lip 53 along one side of the base sheet 52 by a hinge 62. The other perimeter portions of the upper sheet 54 include a channel 64 that can be fitted over the lip 53. The upper sheet 54 is movable from a first, closed position (solid line position in FIGS. 7, 7A and 8) where a user can stand on the sheet 54 to a second, open position (dotted line position shown in FIGS. 7 and 7A) where access can be had to the reservoir 56 for purposes of cleaning. If desired, the upper sheet 54 can be supported by means of protuberances 66 similar to the protuberances 30 extending upwardly from the upper surface 14 of the base sheet 12.

A plurality of suction cups 68 can be attached to the underside of the base sheet 52 in order to prevent slippage of the receptacle 50. Alternatively, as described previously, the underside of the base sheet 52 can be provided with nubs or it can be formed in a hollow configuration which can be provided with a rigidified foam core. Either approach will prevent slippage of the receptacle 50, particularly if a non-slip substance is applied. Yet an additional technique to prevent slippage of the receptacles 10, 50 is to attach stabilizing bars (not shown) to the base of the operating room table and to both sides of the receptacle. Yet an additional technique for preventing slippage of either receptacle is to place the receptacle atop a moist towel that extends a small distance beyond the perimeter of the base sheet 12, 52.

Typically, the device 10, 50 according to the invention will be rectangular in plan view, with dimensions approximately 33.0 inches by 25.0 inches, although larger or smaller dimensions are possible. The thickness of the base sheets 12, 52 is about 0.25 inch. The lips 18, 53 are about 1.125 inches high. In larger versions, the lips 18, 53 may have to be higher in order to maintain a sufficient slope in the floor to provide an adequate flow of fluid. The number and placement of the protuberances 30, 66 can be selected as desired to adequately support the grid 32 and the mat 34 or the upper sheet 54 without affecting fluid flow and without causing difficulties in cleaning. The number and placement of the suction cups 68 can be selected as desired. The number and placement of the suction cups 68 must be adequate to prevent slippage and to provide stable support. However, the use of too many suction cups 68 may cause excessive difficulty in lifting the device from the floor for purposes of being cleaned or repositioned.

As will be apparent from the foregoing description, the present invention provides an effective technique for collecting and removing fluids, particularly fluids that may be present during the course of an arthroscopic surgery procedure. The device is quite sturdy and is capable of being reused many times. It is expected that the device in its various embodiments can be positioned securely on the floor with little concern that slippage will occur. Due to the use of sheet-like construction materials, significant components of the device can be manufactured quickly and inexpensively in an injection molding operation.

Although the invention has been described in its preferred form with a certain degree of particularity, it will be understood that the present disclosure of the preferred embodiment has been made only by way of example and that various changes may be resorted to without departing from the true spirit and scope of the invention as hereinafter claimed. It is intended that the patent shall cover, by suitable expression in the appended claims, whatever features of patentable novelty exist in the invention disclosed.

What is claimed is:

1. A fluid-collecting receptacle for collecting fluid, comprising:

a base sheet formed of a fluid-impervious material having upper and lower surfaces, an upstanding perimeter lip, a sloping floor, and a fluid outlet in the floor;

an upper sheet formed of a fluid-impervious material spaced from the upper surface of the base sheet so as to define a reservoir therebetween; and the upper sheet including a plurality of small basins each with a drain opening at the lowest point thereof through which fluid can be discharged into the reservoir, the upper sheet being hingedly connected to the perimeter lip along one edge, the upper sheet resting atop the remaining portions of the lip, the upper sheet being movable from a first, closed position where a user can stand on the upper sheet to a second, open position where access can be had to the underside of the upper sheet and the upper surface of the base sheet.

2. The fluid-collecting receptacle of claim 1, wherein the base sheet includes a plurality of protuberances projecting upwardly, the upper surfaces of the protuberances lying in a common plane, the upper sheet resting on the protuberances.

3. The fluid-collecting receptacle of claim 1, wherein the base sheet and the upper sheet are made of a plastics material.

4. The fluid-collecting receptacle of claim 1, further comprising suction cups attached to the lower surface of the base sheet.

5. The fluid-collecting receptacle of claim 1, wherein the base sheet is formed of planar sections that converge so as to funnel fluid to the fluid outlet.

6. The fluid-collecting receptacle of claim 1, wherein the lower surface of the base sheet defines a cavity, and further comprising a rigidified foam core filling the cavity.

7. The fluid-collecting receptacle of claim 1, further comprising a non-slip substance applied to the exposed surface of the upper sheet.

8. The fluid-collecting receptacle of claim 1, further comprising nubs formed on the lower surface of the base sheet, the nubs spacing the base sheet a short distance above the surface on which the base sheet rests.

\* \* \* \* \*